United States Patent
Gertsen

(10) Patent No.: US 7,913,564 B2
(45) Date of Patent: Mar. 29, 2011

(54) ULTRASONIC SCANNING DEVICE WITH A HYBRID CONTROLLER

(75) Inventor: Martin Gertsen, Irvington, NY (US)

(73) Assignee: Risk Management Enterprises, LLC, New York, NY (US)

( * ) Notice: Subject to any disclaimer, the term of this patent is extended or adjusted under 35 U.S.C. 154(b) by 435 days.

(21) Appl. No.: 12/046,681

(22) Filed: Mar. 12, 2008

(65) Prior Publication Data

US 2009/0229366 A1    Sep. 17, 2009

(51) Int. Cl.
*G01N 29/265* (2006.01)
*A61B 8/00* (2006.01)

(52) U.S. Cl. .......................................... 73/634; 73/620

(58) Field of Classification Search ............... 73/634, 73/618–620; 600/445, 459
See application file for complete search history.

(56) References Cited

U.S. PATENT DOCUMENTS

| | | | | |
|---|---|---|---|---|
| 3,369,415 A * | 2/1968 | Slawsky | ...................... | 74/89.22 |
| 4,055,988 A * | 11/1977 | Dutton, Jr. | ...................... | 73/620 |
| 4,521,764 A * | 6/1985 | Burton | .......................... | 341/138 |
| 4,841,978 A * | 6/1989 | Eventoff et al. | .............. | 600/445 |
| 4,913,158 A * | 4/1990 | Kikuchi et al. | .............. | 600/446 |
| 6,069,464 A * | 5/2000 | Wu | ................ | 318/610 |
| 2009/0234232 A1* | 9/2009 | Gertsen | ........................ | 600/459 |

* cited by examiner

*Primary Examiner* — Jacques M Saint Surin
(74) *Attorney, Agent, or Firm* — Gottlieb, Rackman & Reisman, P.C.

(57) ABSTRACT

An ultrasonic scanner includes an assembly mounted within a housing and pivoting between two positions. The assembly includes an ultrasonic module that generates an ultrasonic beam directed at a target, such a tissue and detecting the corresponding return beam. A worm screw with a block contacting the assembly is used to selectively pivot the assembly to a desired position. The worm screw is driven by a DC motor and the position of the assembly is monitored using a proximity sensor, such as a Hall Effect Device. A hybrid controller receives analog signals from the Hall Effect Device converts them into corresponding sensor digital signals, and uses them as a feedback signal to an analog OP AMP driving the DC motor.

11 Claims, 4 Drawing Sheets

ULTRASONIC SCANNING DEVICE WITH A HYBRID CONTROLLER

RELATED APPLICATIONS

None

BACKGROUND OF THE INVENTION

A. Field of Invention

This invention pertains to an ultrasonic scanner incorporating a linear scanning device, and more particularly, a scanning device with a hybrid analog-digital controller incorporating a Hall effect device as a feedback or position sensor and a DC motor.

B. Description of the Prior Art

Many electronic instruments include an element or component that is moved or positioned very accurately in order to insure that a desired parameter is measured properly, that a mechanical or electromagnetic force is applied at a desired location or that a physical phenomenon is measured properly. For example, ultrasonic scanner devices typically include an ultrasonic transducer that directs an ultrasonic beam at biological tissues or other samples of interest and a detector that detects the ultrasonic beam reflected from various layers within the tissues or samples. The resulting signals are then analyzed and information is produced about various aspects of the tissues, or sample, such as, for example, their internal structure. Normally, information is sought for not just a single point within the tissues but with regard to a whole area or zone. In order to obtain this information, it is necessary to move the transducer and the detector by a predetermined distance. Often in such a situation, a scanning operation is performed wherein a signal is obtained when the transducer and the detector are at a predetermined location, the transducer and detector are moved by a small amount and a new signal is obtained. This process can be repeated numerous times until the whole area or zone of interest within the tissue or sample has been scanned.

There are many prior art scanners that obtain information about tissue structures and other similar information by using the scanning operation described above. The scanning operation could be accomplished using either analog or digital techniques. Purely analog techniques may not be ideal for this type of operation because they may not be accurate enough, especially if the incremental movement required is very small. That is why existing devices (such as the transducers available from Capistrano Labs, Inc., San Clemente, Calif. 92672) use a digital scheme requiring stepping motors, digital resolvers and other expensive and complicated precision components.

The present inventor has discovered that this problem is solved by using a hybrid analog/digital control scheme, as described below.

SUMMARY OF THE INVENTION

Briefly, an ultrasonic scanner constructed in accordance with this invention includes an elongated assembly having one end pivotably mounted by a hinge in a housing and supporting an ultrasonic module at a second end. The ultrasonic module generates a beam of ultrasonic sound pulses in a direction parallel with the longitudinal axis of the assembly, and the echoing sounds are detected and used to generate information about a tissue or other sample or target of interest. More particularly, the echoing sounds detected by the module are used to generate a two-dimensional image of the target. In a preferred embodiment, in the subject apparatus, the ultrasonic transducer module is placed at several predetermined points that are equidistant from each other and are disposed generally along a trajectory normal to the axis of the module. At each point a two-dimensional image is obtained as described above. In this manner a plurality of two-dimensional images are collected, which can then be combined to generate a three-dimensional image.

A mechanism with a hybrid controller is used to pivot the assembly. The mechanism includes a worm screw disposed in the housing. One end of the worm screw is engaged by a small DC motor so that the worm screw can be selectively turned in one direction or another around its longitudinal axis. The other end of the worm screw passes through a threaded hole in a block. The block is restrained within the housing so that it can be translated or reciprocated along the axis of the worm screw as the screw is turned in one direction or another. The axes of the assembly and the worm screw are disposed at an angle and a side surface of the block is in contact with a side surface of the assembly. As a result, as the worm screw turns and translates the block, the block causes the assembly to move in a camming action.

The position of the assembly is monitored using a position sensor that may be a proximity sensor, preferably incorporating a Hall effect device and a magnet. This device generates a signal that is indicative but not normally linearly proportional to a distance between two elements of the assembly.

A hybrid controller is used to operate the motor. The controller includes an analog operational amplifier and a translator that receives the signal from the position detector and translates into a corresponding signal indicative of actual distance. The controller receives a command to pivot the assembly to a certain position. This command and the output of the translator are fed to the operational amplifier which then activates the motor and pivots the assembly until the desired position is reached.

DETAILED DESCRIPTION OF THE INVENTION

Figure 1:
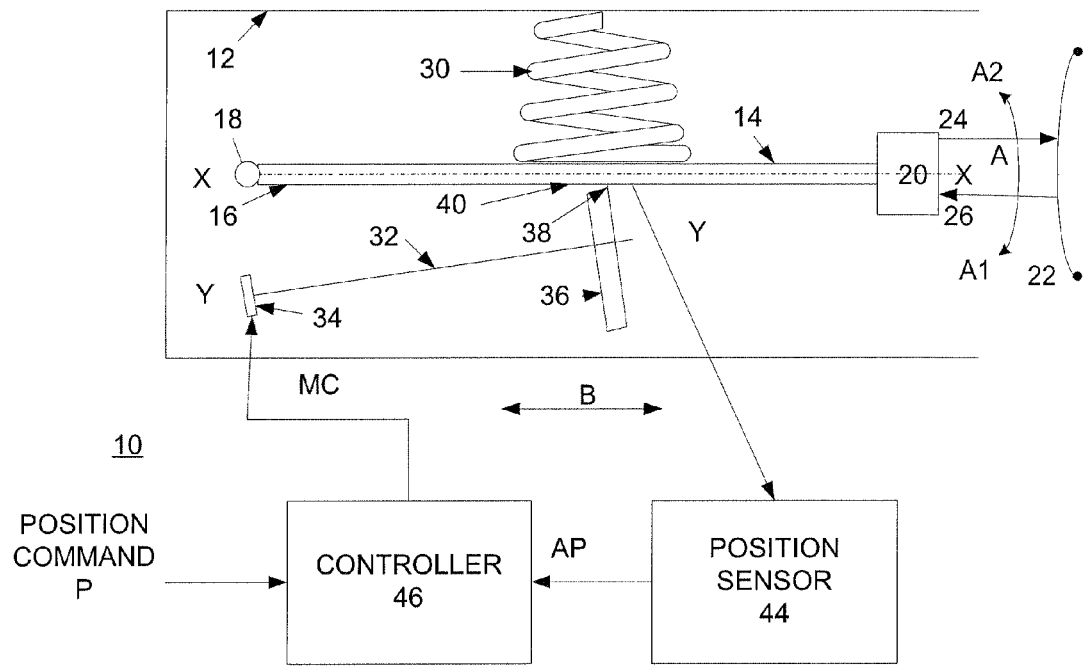
FIG. 1 shows a somewhat diagrammatic view of an ultrasonic scanner constructed in accordance with this invention.

In FIG. 1, for the sake of clarity, a very diagrammatic side view of an ultrasonic scanner constructed in accordance with this invention is presented. The scanner 10 includes a housing 12 with a rod-shaped ultrasonic assembly 14. The assembly 14 is pivotably attached at one end 16 to the housing 12 by a hinge 18. At the opposite end, the assembly 14 has a head 20. The hinge 18 allows the head to move or pivot along an arc A extending between points A1 and A2 as it is disposed near a target such as tissue 22 or other sample of interest. The head 20 includes an ultrasonic module including an ultrasonic source (not shown) that generates short ultrasonic pulses 24 toward the tissue 22. The module further includes a detector (not shown) that detects the echoing pulses 26 returned from the tissue 22. The signals from the detector are then analyzed using known methods which do not pertain to the present invention, and, accordingly, shall not be described.

A biasing spring 30 is disposed between a sidewall of the housing 12 and the assembly 14. This spring biases the assembly 14 so that its longitudinal axis X-X passes through point A1. The purpose of the present invention is to selectively deflect the assembly from this first position toward any intermediate point desired. The furthest that the assembly 14 can travel is the angle at which its axis X-X passes through point A2. For this purpose, the scanner 10 is provided with a worm screw or lead screw 32 having a longitudinal axis Y-Y. (For the purpose of clarity, in FIG. 1, only the axis of the worm screw is shown). The ends of the worm screw 32 are supported so that the axis Y-Y within the housing 12 remains fixed. One end of the worm screw 32 is engaged by a motor 34. The motor 34 is provided to rotate the worm screw 32 selectively clockwise or counterclockwise about axis Y-Y.

A block 36 with a threaded hole (not shown) is mounted on the worm screw 32 and is captured by guides (not shown) that limit the block 36 to a translational or reciprocating movement, as indicated by arrow B. That is, when the worm screw 32 is turned in one way, the block 36 moves to the right along arrow B, when the worm screw is turned the other way, the block 36 moves linearly in the opposite direction. In this manner, the rotational movement of the worm screw 32 is transformed into a translational or reciprocating movement of block 36.

The block 36 has a lateral contact surface 38 facing and contacting a side surface 40 of the assembly 14. The spring 30 pushes the assembly 14 and its contact surface 40 against the contact surface 38. Because the two axes X-X and Y-Y are disposed at an angle, the block 36 and the spring 30 cooperate to cause the assembly 14 to pivot in one direction or another, depending on whether the block 36 moves to the left or the right. Thus the block 36, worm screw 32 and motor 34 together form a pivoting mechanism for pivoting the assembly 14 around hinge 18 by generating a camming force between the contact surfaces 38 and 40.

The position of the assembly 14 can be determined in many different ways. For example, the angular position of the worm screw 32 is directly related to this position. However, the assembly position can be determined more accurately using an active sensor. For example, the device 10 can include a position sensor 44 which determines the position of the assembly 14 with respect to a predetermined reference point and generates an appropriate position signal.

The device 10 generally operates as follows. A controller 46 receives a position command from an external source not shown. The controller 46 also receives a position signal from the position sensor 44 and it compares this signal to the position command. The controller then sends an appropriate control signal to motor 34. The motor 34 turns the worm screw 32 either clockwise or counterclockwise depending on whether the assembly 14 has to pivot towards point A1 or A2. The rotation of the worm screw causes the block 34 to move in the appropriate direction thereby causing the assembly 14 to pivot. The position of the assembly 14 is detected and indicated by the position sensor 44. When the desired position, i.e., the position requested by the position command is reached, the controller cuts off the control signal to the motor 34 and the motor 34, block 36 and assembly 14 stop moving.

Figure 2:
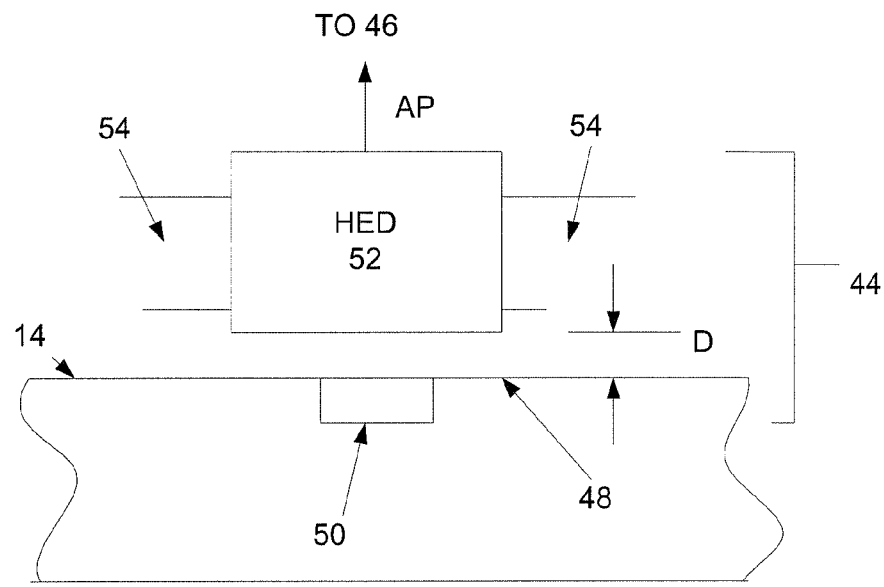
FIG. 2 shows a proximity sensor used for the scanner in FIG. 1.
Figure 3:
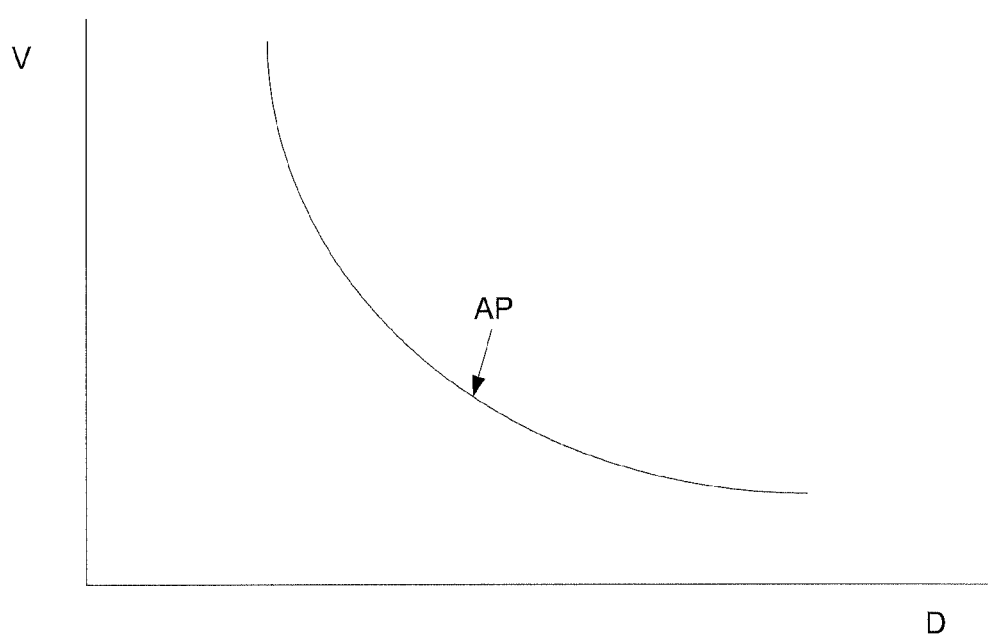
FIG. 3 shows the response of the sensor of FIG. 2.

The position sensor 44 can be implemented in a number of different ways. The present inventor has found that a Hall effect device (HED) is particularly useful for this purpose. A sensor using such a device is illustrated in FIG. 2. In this figure, a surface 48 of assembly 14 is provided with a magnet 50. The magnet can be attached to the surface 48 or it can be imbedded in it. An HED 52 is disposed adjacent to the magnet 50 and is affixed to the housing 12 by a pair of brackets 54 or other similar means. The HED 52 sends an analog position signal AP to the controller 46. As is well known in the field, the signal AP generated by the HED 52 is generally a function of the distance D between the HED 52 and magnet 50. In fact, a typical HED 52 generates a voltage output (that is, signal AP) that is a hyperbolic function of the distance D as shown in FIG. 3. Other proximity sensors may also be used, instead of one using an HED. Moreover, the sensor can be used to measure the distance D directly, as shown in FIG. 2, or indirectly, for example by measuring the position or movement of the block 36.

Figure 4:
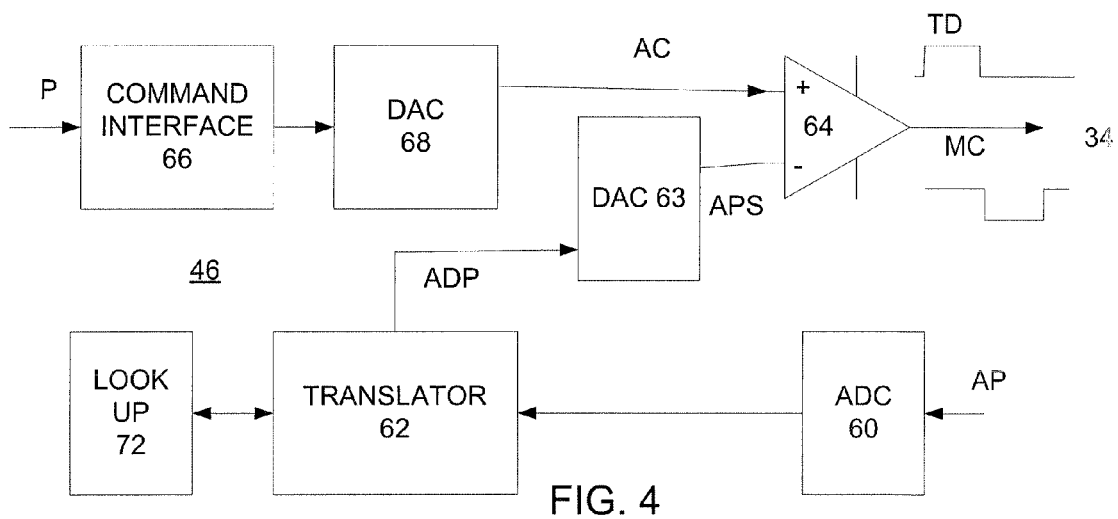
FIG. 4 shows a block diagram of the hybrid control scheme used in the scanner of FIG. 1.

FIG. 4 shows a block diagram of the controller 46. The controller 46 includes an A/D converter 60 that receives the signal AP and converts it to a corresponding digital signal. The digital signal is then provided to a translator 62. The purpose of the translator 62 is to provide an adjusted position signal ADP. This adjusted position signal is generated using a translation function corresponding to the curve of FIG. 3. In other words, the signal ADP is a digital signal that indicates the actual position of the assembly 14 based on the signal AP from the HED 52. This signal ADP is converted to an analog position signal APS by D/A converter 63 and fed to the inverting input of an operational amplifier (OPAMP) 64. OPAMP 64 is a standard analog amplifier that that is provided with various standard biasing and filtering circuits designed to insure that the OPAMP 64 has a limited gain at low frequencies. A method of determining the function used by the translator 62 is described below.

The controller 46 also includes a command interface 66 receiving a position command P. This command P is preferably received from a PC, a user interface, or any other source and is usually a digital signal and is converted into an analog command AC, and this command AC is then fed to the non-inverting input of OPAMP 64. The OPAMP 64 compares the two signals AC and APS and generates a motor control signal MC that is either a positive pulse if this difference indicates that the motor 34 has to turn in one direction or a negative pulse if the motor has to turn in the other direction. The rotation of the motor causes the assembly 14 to pivot to the position requested by the position command P. The position of the assembly 14 is tracked by the HED 52. When the requested position is reached, the difference between signals AC and APS is zero and the output of OPAMP 64 drops to zero as well. Thus, the duration TD of the pulse is equal to the time that it takes for the assembly 14 to pivot from an initial position to the requested position.

The translator 62 is preferably an ASIC chip or other similarly custom made element. It can be set to perform in several different ways. The easiest, but perhaps not the most reliable way is to use the published specs that are provided by the manufacturer of the HED 42. A more reliable way is to have the motor 34, block 36 and assembly 14 cooperate to pivot one or more times between points A1, A2 with stops at several intermediate points therebetween. At each intermediate point, the distance D and the corresponding voltage AP output by the HED are measured and recorded. A curve fitting program is then used to determine the function correlating the voltage AP to the distance D. As indicated above, this function is normally a hyperbolic curve. The function is then programmed into the translator 62, and each time the translator 62 receives a signal AP, it is translated into corresponding signal ADP.

Yet another approach is to repeat the process described above, but instead of generating a function, a look-up table 72 can be created. In this implementation, for each value AP, the translator 62 looks up the corresponding signal ADP in a look-up table 72.

Of course, strictly speaking, the distance D detected by device 52 is not the important parameter. The important parameter is the distance that head 20 moves as a result of the rotation of the worm screw 32. However, this latter distance is proportional to distance D and therefore, the translator 62 automatically scales distance D accordingly. For example, if the device 52 is disposed at the middle of the assembly 16, the distance D is automatically doubled.

As mentioned above, the device 10 is an ultrasonic scanner, and as such can be used in several different ways. One way is to point it at a particular direction using the position command and then obtain a two-dimensional picture of the target with head 20. However, a more common practice is to scan the tissue or other target and generate a plurality of two-dimensional images which can be converted into a corresponding 3-D image. For this purpose, commands can be generated, for example, from a PC to, move the assembly 14 so that it is pointing at A1. Then assembly 14 can be sequentially pivoted to many intermediate positions between A1 and A2 and ultrasonic signals can be collected at each. For this operation, the controller 46 can be connected to a standard PC which then generates the positioning commands sequentially. A standard connection can be used for this purpose, such as a USB connector. For a typical 3-D ultrasonic image the head 12 is moved 5 mm in increments of 10μ. The device 10 performs this operation very fast and accurately.

Figure 5:
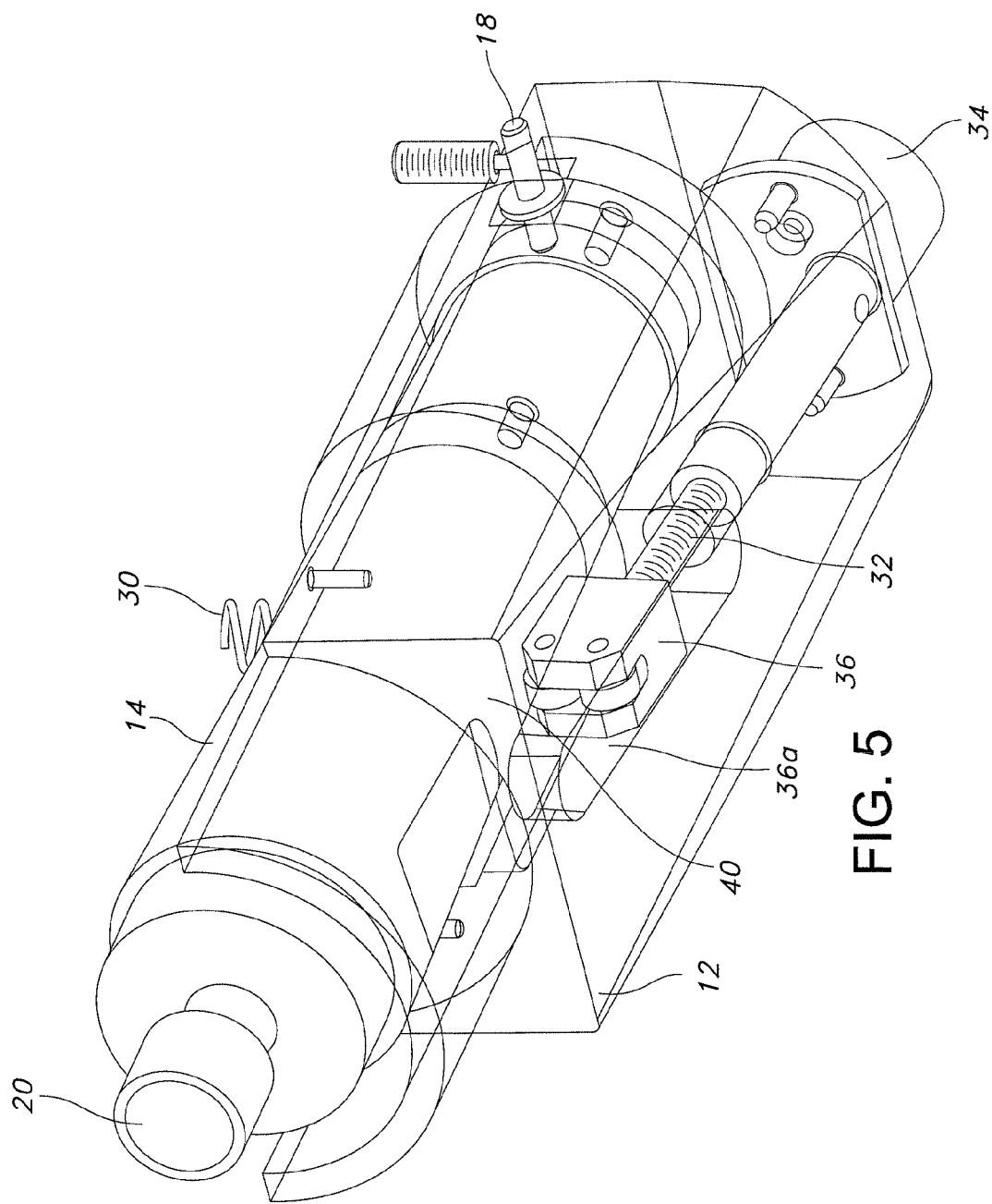
FIG. 5 shows a first isometric view of the ultrasonic scanner of FIG. 1 with portions cut out to show the inner elements thereof.
Figure 6:
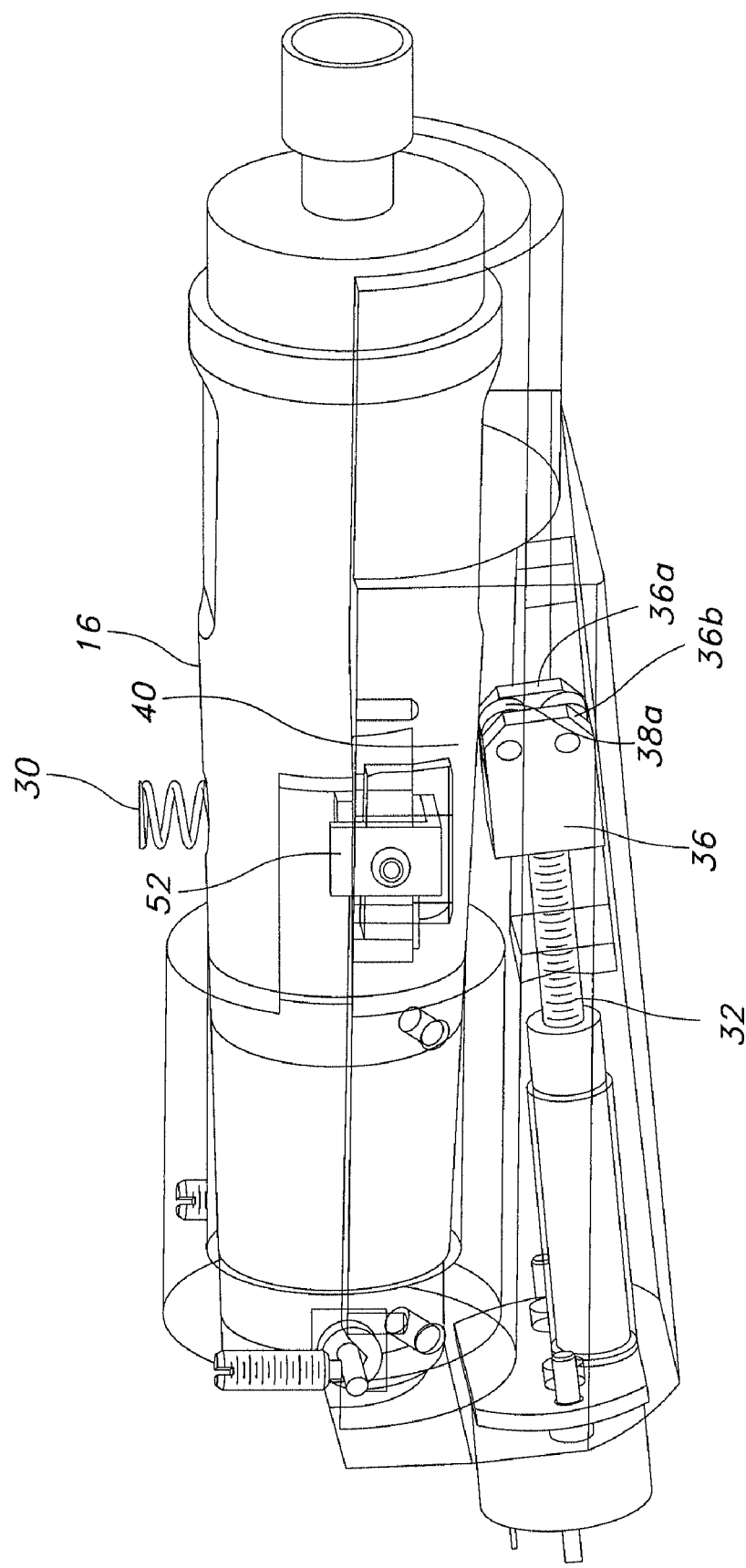
FIG. 6 shows a second isometric view of the ultrasonic scanner of FIG. 1.

In FIGS. 1 and 2, the device 10 is illustrated somewhat diagrammatically, with many elements being omitted, and other elements being shown with disproportionate dimensions. In FIGS. 5 and 6 the device 10 is represented more realistically. As illustrated in these figures, the block 36 is accommodated in a guide 36A which limits its movement to a linear motion. In other words, guide 36A insures that the block 36 does not rotate with worm screw 32.

In addition, as is clear from these drawings, preferably, the block 36 is provided with two rollers 38A and 36B. Roller 38A provides the contact with surface 40 of the assembly 16. In this manner, frictional forces between the block 36 and assembly 16 are reduced considerably to insure that the motion of block 36 is transmitted smoothly to the assembly 16 and to reduce wear and tear on these elements. Similarly roller 36B eliminates or reduces friction between the block 36 and its guide 36A.

Numerous modifications may be made to this invention without departing from its scope as defined in the appended claims.

I claim:

1. An ultrasonic scanner comprising:
a housing;
an assembly having an elongated body pivotably attached to the housing at one end, and having an ultrasonic module at the other end and a contact surface there between said ultrasonic module selectively generating signals characterizing a target;
a pivoting mechanism including a worm screw disposed in the housing, a motor selectively rotating said worm screw and a block mounted on the worm screw, said block being driven linearly when the worm screw is rotated, said block engaging said contact surface to cause said assembly to pivot about said one end;
a controller including a position sensor for sensing the position of the assembly and generating an output based on said position of the assembly for driving said motor, wherein said controller receives a digital sensor signal based on said output from said sensor; and
a translator that translates said digital sensor signal into a distance signal, said distance signal being used as a feedback signal by said controller.

2. The ultrasonic scanner of claim 1 wherein said sensor includes a magnet disposed on said assembly and a Hall Effect Device (HED) disposed on said housing and arranged to measure a distance to said assembly.

3. The ultrasonic scanner of claim 2 wherein said controller includes an operational amplifier having a first input receiving a position command and a second input receiving said feedback signal and an output used for driving said motor.

4. The ultrasonic scanner of claim 3 wherein said controller receives a digital position signal and further includes a first D/A converter to convert said digital position signal into said position command.

5. The ultrasonic scanner of claim 4 further comprising a second A/D converter receiving an analog signal from said sensor and generating a digital sensor signal corresponding to said sensor signal.

6. The ultrasonic scanner of claim 2 wherein said translator uses a preset formula to generate said distance signal, said preset formula being related to the physical characteristics of said HED.

7. The ultrasonic scanner of claim 1 wherein said translator includes a look-up table for converting said digital sensor signal into said distance signal.

8. A device comprising:
a housing;
an assembly having a first end pivotably mounted in said housing and a second end disposed opposite said first end;
a sensor detecting a current position of said assembly with respect to said housing;
a pivoting mechanism disposed in said housing for pivoting said assembly with respect to said first end, said pivoting mechanism including an electric motor, a worm screw extending at least partially along said assembly and being selectively rotated about its longitudinal axis by said motor, and a block mounted on said worm screw and arranged to apply a caming force on said assembly to cause it to pivot with respect to said first end; and
a controller receiving an input from said sensor and a command to pivot said assembly, said controller generating a signal to said motor to cause said motor to rotate said worm screw until the signal from said sensor indicates that the required position has been reached;
wherein said sensor includes a magnet supported by one of said housing and said assembly and a Hall Effect Device (HED) on the other of said housing and assembly, said HED generating a sensor signal indicative of the current distance between said assembly and a portion of said housing; and
wherein said controller includes a translator that translates said sensor signal into a distance signal based on the physical characteristics of said HED.

9. The device of claim 8 further comprising an analog amplifier receiving a position command and said distance signal and generating an output signal driving said motor.

10. The device of claim 9 wherein said motor is a DC motor.

11. The device of claim 8 wherein said translator includes a look-up table for translating said sensor signal.

* * * * *